US006965054B2

(12) United States Patent
Oi et al.

(10) Patent No.: US 6,965,054 B2
(45) Date of Patent: Nov. 15, 2005

(54) PROCESS FOR PRODUCING MIXTURE OF DIHYDROXYDIPHENYLSULFONE ISOMERS

(75) Inventors: Fumio Oi, Wakayama (JP); Norio Yanase, Wakayama (JP); Masamichi Yamamoto, Wakayama (JP)

(73) Assignee: Konishi Chemical Ind. Co., Ltd., Wakayama (JP)

( * ) Notice: Subject to any disclaimer, the term of this patent is extended or adjusted under 35 U.S.C. 154(b) by 48 days.

(21) Appl. No.: 10/490,819

(22) PCT Filed: Sep. 26, 2002

(86) PCT No.: PCT/JP02/09920

§ 371 (c)(1),
(2), (4) Date: Mar. 25, 2004

(87) PCT Pub. No.: WO03/029204

PCT Pub. Date: Apr. 10, 2003

(65) Prior Publication Data

US 2004/0254400 A1 Dec. 16, 2004

(30) Foreign Application Priority Data

Sep. 28, 2001 (JP) ............................ 2001-300933
Sep. 28, 2001 (JP) ............................ 2001-300942

(51) Int. Cl.$^{7}$ ............................ C07C 317/33
(52) U.S. Cl. ............................ 568/33
(58) Field of Search ............................ 568/33

(56) References Cited

U.S. PATENT DOCUMENTS 4,996,367 A 2/1991 Ernst et al.
5,767,318 A * 6/1998 Hosoda et al. ................ 568/33

FOREIGN PATENT DOCUMENTS

| | | |
|---|---|---|
| EP | 0 220 004 A1 | 4/1987 |
| EP | 0 461 272 A1 | 12/1991 |
| EP | 0 627 415 A1 | 12/1994 |
| EP | 0 755 920 A1 | 1/1997 |
| JP | 50-116446 A | 9/1975 |
| JP | 10-25277 A | 1/1998 |
| JP | 10-139756 A. | 5/1998 |

OTHER PUBLICATIONS

Yoshihiro Yoshii, et al., "Isomer Distribution in Sulfonation and p-Hydroxyphenylsulfonylation of Phenol," Journal of the Chemical Society of Japan, 1985 (1), pp. 70-74.

* cited by examiner

*Primary Examiner*—Johann Richter
*Assistant Examiner*—Chukwuma Nwaonicha
(74) *Attorney, Agent, or Firm*—Knobbe, Martens, Olson & Bear LLP

(57) ABSTRACT

The present invention provides a process for producing a mixture of dihydroxydiphenylsulfone isomers containing 2,4'-dihydroxydiphenylsulfone, the process comprising heating 4,4'-dihydroxydiphenylsulfone or a mixture of dihydroxydiphenylsulfone isomers containing at least 85 wt. % of 4,4'-dihydroxydiphenylsulfone in the presence of phenol and sulfuric or sulfonic acid.

7 Claims, No Drawings

PROCESS FOR PRODUCING MIXTURE OF DIHYDROXYDIPHENYLSULFONE ISOMERS

This application is the U.S. National Phase under 35 U.S.C. §371 of International Application PCT/JP02/09920, filed Sep. 26, 2002, which claims priority to Japanese Patent Application No. 2001-300933, filed Sep. 28, 2001, and Japanese Patent Application No. 2001-300942, filed Sep. 28, 2001. The International Application was not published under PCT Article 21(2) in English.

TECHNICAL FIELD

The present invention relates to a process for producing a mixture of dihydroxydiphenylsulfone isomers containing 2,4'-dihydroxydiphenylsulfone.

BACKGROUND ART

Among various phenolic compounds, 2,4'-dihydroxydiphenylsulfone (hereinafter occasionally referred to as 2,4'-DDS) has recently attracted attention because of its great utility as a color developer for heat-sensitive paper.

Known methods for producing 2,4'-DDS include the separation and purification of 2,4'-DDS from mixtures containing 2,4'-DDS and 4,4'-dihydroxydiphenylsulfone (hereinafter occasionally referred to as 4,4'-DDS).

Moreover, it is known that when 4,4'-DDS is heated in a phenol solvent in the presence of an acid catalyst, isomerization occurs, thereby producing a mixture of dihydroxydiphenylsulfone isomers containing 4,4'-DDS and 2,4'-DDS in a weight ratio of about 75 to about 25 (isomerization equilibrium) (Journal of the Chemical Society of Japan, 1985 (1), 70–74). However, since this isomerization reaction requires 20 hours or longer to reach isomerization equilibrium even under heating conditions of 190° C. or higher, it is difficult to employ this isomerization reaction industrially.

DISCLOSURE OF THE INVENTION

An object of the invention is to provide a process for producing a mixture of dihydroxydiphenylsulfone isomers containing an enhanced amount of 2,4'-DDS, the process being able to induce isomerization equilibrium in a short period of time when 4,4'-DDS is isomerized.

Other objects and characteristics of the present invention will become evident by the disclosure provided hereinbelow.

The inventors conducted extensive research and found that heating 4,4'-DDS in the presence of specific amounts of phenol and sulfuric acid can induce isomerization equilibrium in a short period of time. The present invention has been accomplished based on this finding.

Furthermore, the inventors found that heating 4,4'-DDS in the presence of phenol and sulfonic acid can induce isomerization equilibrium in a short period of time. The present invention has been accomplished based also on this finding.

In other words, the present invention provides processes for producing a mixture of dihydroxydiphenylsulfone isomers as described below:

1. A process for producing a mixture of dihydroxydiphenylsulfone isomers containing 2,4'-dihydroxydiphenylsulfone, the process comprising heating 4,4'-dihydroxydiphenylsulfone to a temperature of 160° C. or higher in the presence of an equal weight or less of phenol and 20 mol % or less of sulfuric acid relative to the 4,4'-dihydroxydiphenylsulfone.

2. A process for producing a mixture of dihydroxydiphenylsulfone isomers containing 2,4'-dihydroxydiphenylsulfone, the process comprising heating a mixture of dihydroxydiphenylsulfone isomers containing 4,4'-dihydroxydiphenylsulfone in a proportion of at least 85 wt. % to a temperature of 160° C. or higher in the presence of an equal weight or less of phenol and 20 mol % or less of sulfuric acid relative to the mixture.
3. A process for producing a mixture of dihydroxydiphenylsulfone isomers containing 2,4'-dihydroxydiphenylsulfone, the process comprising heating 4,4'-dihydroxydiphenylsulfone in the presence of phenol and sulfonic acid.
4. A process for producing a mixture of dihydroxydiphenylsulfone isomers containing 2,4'-dihydroxydiphenylsulfone, the process comprising heating a mixture of dihydroxydiphenylsulfone isomers containing 4,4'-dihydroxydiphenylsulfone in a proportion of at least 85 wt. % in the presence of phenol and sulfonic acid.

Hereinbelow, the process for producing a mixture of dihydroxydiphenylsulfone isomers of the present invention is described in more detail:

[Process Employing Sulfuric Acid]

As a single starting material of the present invention, 4,4'-DDS may have a purity of 99% or higher.

A mixture of dihydroxydiphenylsulfone isomers containing 4,4'-DDS in a proportion of at least 85 wt. % can also be used as a starting material. It is preferable that this isomeric mixture contains 2,4'-DDS as another isomer.

The starting material, i.e., 4,4'-DDS or a mixture of dihydroxydiphenylsulfone isomers containing 4,4'-DDS in a proportion of at least 85 wt. %, is isomerized by heating in the presence of phenol and sulfuric acid.

Phenol is used in a weight equal to or less than, and preferably in a weight of 0.1 to 0.8 times as much as, the starting material, i.e., 4,4'-DDS or a mixture of dihydroxydiphenylsulfone isomers containing 4,4'-DDS.

Sulfuric acid is used in a proportion of 20 mol % or less, and preferably in a proportion of 1 to 10 mol %, based on the starting material, i.e., 4,4'-DDS or a mixture of dihydroxydiphenylsulfone isomers containing 4,4'-DDS.

Solvents may or may not be used. When solvents are used, heat- and acid-resistant solvents such as sulfolane and the like are preferable.

The reaction temperature for conducting isomerization is 160° C. or higher, and preferably 170 to 210° C. Isomerization can be conducted under pressure as necessary.

The reaction time is not limited. The reaction may be continued until isomerization equilibrium. The preferable reaction time is 0.1 to 15 hours, and more preferable is 0.5 to 10 hours.

The desired product of the present invention, i.e., a mixture of dihydroxydiphenylsulfone isomers containing 2,4'-DDS, is primarily composed of 4,4'-DDS and 2,4'-DDS. Preferable is a mixture containing 2,4'-DDS in a proportion of 15 to 30 wt. %, more preferable is a mixture containing 2,4'-DDS in a proportion of 20 to 30 wt. %, and especially preferable is a mixture containing 2,4'-DDS in a proportion of 22 to 30 wt. %.

2,4'-DDS can be separated from a mixture of dihydroxydiphenylsulfone isomers containing 2,4'-DDS produced according to the invention using known separation and purification methods.

According to the process of the present invention, when 4,4'-DDS is isomerized, isomerization equilibrium is achieved in a short period of time, and a mixture of dihydroxydiphenylsulfone isomers containing an enhanced amount of 2,4'-DDS can be obtained.

[Process Employing Sulfonic Acid]

As a single starting material of the present invention, 4,4'-DDS may have a purity of 99% or higher.

A mixture of dihydroxydiphenylsulfone isomers containing 4,4'-DDS in a proportion of at least 85 wt. % can also be used as a starting material. It is preferable that this isomeric mixture contains 2,4'-DDS as another isomer.

The starting material, i.e., 4,4'-DDS or a mixture of dihydroxydiphenylsulfone isomers containing 4,4'-DDS in a proportion of at least 85 wt. %, is isomerized by heating in the presence of phenol and sulfonic acid.

Phenol is used preferably in a weight twice as much as or less than, and more preferably in a weight 0.1 to 1 times as much as, the starting material, i.e., 4,4' -DDS or a mixture of dihydroxydiphenylsulfone isomers containing 4,4'-DDS.

Examples of sulfonic acids usable in the invention include benzenetrisulfonic acid, benzenedisulfonic acid, chlorobenzenedisulfonic acid, toluenesulfonic acid, phenolsulfonic acid, and like aromatic mono-, di-, or trisulfonic acids; methanesulfonic acid, ethanesulfonic acid, trifluoromethanesulfonic acid, pentafluoroethanesulfonic acid, and like optionally-fluorinated aliphatic sulfonic acids; Nafion® and like polymeric sulfonic acids; etc. Among these sulfonic acids, aromatic mono-, di-, or trisulfonic acids are preferable; and benzenedisulfonic acid, toluenesulfonic acid, and the like are more preferable.

Sulfonic acid is used preferably in a proportion of 20 mol % or lower, and more preferably in a proportion of 1 to 10 mol %, based on the starting material, i.e., 4,4'-DDS or a mixture of dihydroxydiphenylsulfone isomers containing 4,4'-DDS.

Solvents may or may not be used. When solvents are used, heat- and acid-resistant solvents such as sulfolane and the like are preferable.

The reaction temperature for conducting isomerization is preferably 160° C. or higher, and more preferably 170 to 210° C. Isomerization can be conducted under pressure as necessary.

The reaction time is not limited. The reaction may be continued until isomerization equilibrium. The preferable reaction time is 0.1 to 15 hours, and more preferable is 0.5 to 10 hours.

The desired product of the present invention, i.e., a mixture of dihydroxydiphenylsulfone isomers containing 2,4'-DDS, is primarily composed of 4,4'-DDS and 2,4'-DDS. Preferable is a mixture containing 2,4'-DDS in a proportion of 15 to 30 wt. %, more preferable is a mixture containing 2,4'-DDS in a proportion of 20 to 30 wt. %, and especially preferable is a mixture containing 2,4'-DDS in a proportion of 22 to 30 wt. %.

2,4'-DDS can be separated from a mixture of dihydroxydiphenylsulfone isomers containing 2,4'-DDS produced according to the invention using known separation and purification methods.

According to the process of the present invention, when 4,4'-DDS is isomerized, isomerization equilibrium is achieved in a short period of time, and a mixture of dihydroxydiphenylsulfone isomers containing an enhanced amount of 2,4'-DDS can be obtained.

BEST MODE FOR CARRYING OUT THE INVENTION

Examples are given below to illustrate the invention in more detail.

EXAMPLE I-1

To 100 g (0.4 mol) of dihydroxydiphenylsulfone (containing 4,4'-DDS in a proportion of 99.8 wt. % and 2,4'-DDS in a proportion of 0.1 wt. %; hereinafter referred to as bisphenol S (1)) were added 50 g of phenol and 1.6 g (0.016 mol, 4 mol % relative to bisphenol S (1)) of 98% sulfuric acid. The mixture was heated to 195° C. and stirred at this temperature. The results of HPLC (high performance liquid chromatography) analysis conducted after 2 hours of stirring revealed that the mixture contained 4,4'-DDS and 2,4'-DDS in a weight ratio of 85:15, and the mixture after 6 hours of stirring contained 4,4'-DDS and 2,4'-DDS in a weight ratio of 76:24.

EXAMPLE I-2

To 100 g of bisphenol S (1) were added 50 g of phenol and 4 g (0.04 mol, 10 mol % relative to bisphenol S (1)) of 98% sulfuric acid. The mixture was heated to 180° C. and stirred at this temperature. The results of HPLC analysis conducted after 2 hours of stirring revealed that the mixture contained 4,4'-DDS and 2,4'-DDS in a weight ratio of 86:14, and the mixture after 6 hours of stirring contained 4,4'-DDS and 2,4'-DDS in a weight ratio of 76:24.

EXAMPLE I-3

To 100 g of bisphenol S (1) were added 50 g of phenol and 4 g (0.04 mol, 10 mol % relative to bisphenol S (1)) of 98% sulfuric acid. The mixture was heated to 210° C. and stirred at this temperature. The results of HPLC analysis conducted after 1 hour of stirring revealed that the mixture contained 4,4'-DDS and 2,4'-DDS in a weight ratio of 75:25, and the mixture after 2 hours of stirring contained 4,4'-DDS and 2,4'-DDS in a weight ratio of 73:27.

EXAMPLE I-4

To 100 g (0.4 mol) of dihydroxydiphenylsulfone (containing 4,4'-DDS in a proportion of 86 wt. % and 2,4'-DDS in a proportion of 14 wt. %; hereinafter referred to as bisphenol S (2)) were added 50 g of phenol and 1.6 g (0.016 mol, 4 mol % relative to bisphenol S (2)) of 98% sulfuric acid. The mixture was heated to 195° C. and stirred at this temperature. The results of HPLC analysis conducted after 2 hours of stirring revealed that the mixture contained 4,4'-DDS and 2,4'-DDS in a weight ratio of 79:21, and the mixture after 6 hours of stirring contained 4,4'-DDS and 2,4'-DDS in a weight ratio of 75:25.

COMPARATIVE EXAMPLE I-1

To 15 g (0.06 mol) of bisphenol S (1) were added 36 g of phenol and 3 g (0.03 mol, 50 mol % relative to bisphenol S (1)) of 98% sulfuric acid. The mixture was heated to 195° C. and stirred at this temperature. The results of HPLC analysis conducted after 2 hours of stirring revealed that the mixture contained 4,4'-DDS and 2,4'-DDS in a weight ratio of 88:12, the mixture after 6 hours of stirring contained 4,4'-DDS and 2,4'-DDS in a weight ratio of 82:18, and the mixture after 20 hours of stirring contained 4,4'-DDS and 2,4'-DDS in a weight ratio of 78:22.

EXAMPLE II-1

To 100 g (0.4 mol) of bisphenol S (1) were added 100 g of phenol and 5 g (0.02 mol, 5 mol % relative to bisphenol S (1)) of benzenedisulfonic acid. The mixture was heated to 180° C. and stirred at this temperature. The results of HPLC analysis conducted after 2 hours of stirring revealed that the mixture contained 4,4'-DDS and 2,4'-DDS in a weight ratio of 81:19, and the mixture after 6 hours of stirring contained 4,4'-DDS and 2,4'-DDS in a weight ratio of 77:23.

EXAMPLE II-2

To 100 g of bisphenol S (1) were added 50 g of phenol and 3 g (0.017 mol, 4 mol % relative to bisphenol S (1)) of toluenesulfonic acid. The mixture was heated to 195° C. and stirred at this temperature. The results of HPLC analysis conducted after 2 hours of stirring revealed that the mixture contained 4,4'-DDS and 2,4'-DDS in a weight ratio of 79:21, and the mixture after 6 hours of stirring contained 4,4'-DDS and 2,4'-DDS in a weight ratio of 75:25.

EXAMPLE II-3

To 100 g of bisphenol S (1) were added 50 g of phenol and 6.9 g (0.04 mol, 10 mol % relative to bisphenol S (1)) of toluenesulfonic acid. The mixture was heated to 180° C. and stirred at this temperature. The results of HPLC analysis conducted after 2 hours of stirring revealed that the mixture contained 4,4'-DDS and 2,4'-DDS in a weight ratio of 86:14, and the mixture after 6 hours of stirring contained 4;4'-DDS and 2,4'-DDS in a weight ratio of 76:24.

EXAMPLE II-4

To 100 g of bisphenol S (1) were added 50 g of phenol and 6.9 g (0.04 mol, 10 mol % relative to bisphenol S (1)) of toluenesulfonic acid. The mixture was heated to 210° C. and stirred at this temperature. The results of HPLC analysis conducted after 1 hour of stirring revealed that the mixture contained 4,4'-DDS and 2,4'-DDS in a weight ratio of 75:25, and the mixture after 2 hours of stirring contained 4,4'-DDS and 2,4'-DDS in a weight ratio Of 73:27.

EXAMPLE II-5

To 100 g (0.4 mol) of bisphenol S (2) were added 50 g of phenol and 3 g (0.017 mol, 4 mol % relative to bisphenol S (2)) of toluenesulfonic acid. The mixture was heated to 195° C. and stirred at this temperature. The results of HPLC analysis conducted after 2 hours of stirring revealed that the mixture contained 4,4'-DDS and 2,4'-DDS in a weight ratio of 77:23, and the mixture after 6 hours of stirring contained 4,4'-DDS and 2,4'-DDS in a weight ratio of 75:25.

COMPARATIVE EXAMPLE II-1

To 15 g (0.06 mol) of bisphenol S (1) were added 36 g of phenol and 3 g (0.03 mol, 50 mol % relative to bisphenol S (1)) of 98% sulfuric acid. The mixture was heated to 195° C. and stirred at this temperature. The results of HPLC analysis conducted after 2 hours of stirring revealed that the mixture contained 4,4'-DDS and 2,4'-DDS in a weight ratio of 88:12, the mixture after 6 hours of stirring contained 4,4'-DDS and 2,4'-DDS in a weight ratio of 82:18, and the mixture after 20 hours of stirring contained 4,4'-DDS and 2,4'-DDS in a weight ratio of 78:22.

What is claimed is:

1. A process for producing a mixture of dihydroxydiphenylsulfone isomers containing 2,4'-dihydroxydiphenylsulfone, the process comprising heating 4,4'-dihydroxydiphenylsulfone to a temperature of 160° C. or higher in the presence of an equal weight or less of phenol and 20 mol % or less of sulfuric acid relative to the 4,4'-dihydroxydiphenylsulfone.

2. A process for producing a mixture of dihydroxydiphenylsulfone isomers containing 2,4'-dihydroxydiphenylsulfone, the process comprising heating a mixture of dihydroxydiphenylsulfone isomers containing 4,4'-dihydroxydiphenylsulfone in a proportion of at least 85 wt. % to a temperature of 160° C. or higher in the presence of an equal weight or less of phenol and 20 mol % or less of sulfuric acid relative to the mixture.

3. A process for producing a mixture of dihydroxydiphenylsulfone isomers containing 2,4'-dihydroxydiphenylsulfone, the process comprising heating 4,4'-dihydroxydiphenylsulfone in the presence of phenol and sulfonic acid.

4. A process for producing a mixture of dihydroxydiphenylsulfone isomers containing 2,4'-dihydroxydiphenylsulfone, the process comprising heating a mixture of dihydroxydiphenylsulfone isomers containing 4,4'-dihydroxydiphenylsulfone in a proportion of at least 85 wt. % in the presence of phenol and sulfonic acid.

5. A process for producing a mixture of dihydroxydiphenylsulfone isomers containing 2,4'-dihydroxydiphenylsulfone, comprising:

providing, as a single starting material, 4,4'-dihydroxydiphenylsulfone or a mixture of dihydroxydiphenylsulfone isomers containing 4,4'-dihydroxydiphenylsulfone in a proportion of at least 85 wt. %; and heating the starting material to a temperature of 160° C. or higher in the presence of phenol in an amount equal to or less than the starting material by weight and sulfuric acid in an amount of 20 mol % or less relative to the starting material to isomerize the starting material, thereby obtaining a mixture of dihydroxydiphenylsulfone isomers containing 2,4'-dihydroxydiphenylsulfone.

6. The process according to claim 5, wherein the mixture of dihydroxydiphenylsulfone isomers contains 2,4'-dihydroxydiphenylsulfone in an amount 15–30 wt. %.

7. The process according to claim 5, wherein the starting material is heated to 170–210° C.

* * * * *